(12) United States Patent
Onuma et al.

(10) Patent No.: US 12,053,222 B2
(45) Date of Patent: Aug. 6, 2024

(54) TREATMENT SYSTEM

(71) Applicant: Olympus Corporation, Hachioji (JP)

(72) Inventors: Ryu Onuma, Hachioji (JP); Kenichi Kimura, Hachioji (JP); Tsunetaka Akagane, Hachioji (JP); Satoshi Honda, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 396 days.

(21) Appl. No.: 16/722,344

(22) Filed: Dec. 20, 2019

(65) Prior Publication Data

US 2020/0121380 A1   Apr. 23, 2020

Related U.S. Application Data

(63) Continuation of application No. PCT/JP2017/024343, filed on Jul. 3, 2017.

(51) Int. Cl.
| | | |
|---|---|---|
| *A61B 18/12* | (2006.01) | |
| *A61B 18/00* | (2006.01) | |
| *A61B 18/14* | (2006.01) | |

(52) U.S. Cl.
CPC .... *A61B 18/12* (2013.01); *A61B 2018/00708* (2013.01); *A61B 2018/00755* (2013.01); *A61B 2018/1452* (2013.01)

(58) Field of Classification Search
CPC .......... A61B 18/12; A61B 2018/00708; A61B 2018/0755; A61B 2018/1452
See application file for complete search history.

(56) References Cited

U.S. PATENT DOCUMENTS

| | | | |
|---|---|---|---|
| 2010/0042101 A1 | 2/2010 | Inagaki et al. | |
| 2011/0112400 A1* | 5/2011 | Emery | A61N 7/00 601/3 |

(Continued)

FOREIGN PATENT DOCUMENTS

| | | |
|---|---|---|
| JP | 2001-120566 A | 5/2001 |
| JP | 2005-000224 A | 1/2005 |

(Continued)

OTHER PUBLICATIONS

Jan. 7, 2020 International Preliminary Report on Patentability issued in International Patent Application No. PCT/JP2017/024343.

(Continued)

*Primary Examiner* — Eun Hwa Kim
*Assistant Examiner* — Catherine C. Premraj
(74) *Attorney, Agent, or Firm* — Oliff PLC

(57) ABSTRACT

The disclosed technology is directed to a treatment system comprises a power supply apparatus and a treatment instrument configured to communicate electrically with the power supply apparatus so as to perform a treatment on a biological tissue. The treatment instrument includes an end effector that transmits a high-frequency current delivered by a first electrical energy to the biological tissue. An electric element is configured to operate the end effector by being actuated using second electric energy. The power supply apparatus includes a processor configured to receive a stop command to cutoff the supply of the first electric energy and the second electric energy in a state in which the first electric energy and the second electric energy are supplied and determine whether or not the end effector is in contact with the biological tissue based on a parameter related to the first electric energy after receiving the stop command.

15 Claims, 7 Drawing Sheets

(56) References Cited

U.S. PATENT DOCUMENTS

| 2013/0190660 | A1 | 7/2013 | Tanaka et al. |
| 2014/0180274 | A1* | 6/2014 | Kabaya .............. A61B 18/1445 606/34 |
| 2014/0194868 | A1 | 7/2014 | Sanai et al. |
| 2014/0276715 | A1* | 9/2014 | Shuman ................ A61B 18/04 606/28 |
| 2015/0165238 | A1* | 6/2015 | Slayton .............. A61B 18/1815 601/2 |
| 2017/0245917 | A1 | 8/2017 | Sugawara |

FOREIGN PATENT DOCUMENTS

| JP | 2010-042249 A | 2/2010 |
| WO | 2013/042498 A1 | 3/2013 |
| WO | 2013/157571 A1 | 10/2013 |
| WO | 2016/203867 A1 | 12/2016 |

OTHER PUBLICATIONS

Sep. 19, 2017 International Search Report issued in International Patent Application No. PCT/JP2017/024343.

* cited by examiner

TREATMENT SYSTEM

CROSS-REFERENCE TO RELATED APPLICATION

This application is a continuation application of PCT Application No. PCT/JP 2017/024343 filed on Jul. 3, 2017, which is hereby incorporated by reference in its entirety.

TECHNICAL FIELD

The disclosed technology relates to a power supply apparatus for use in conjunction with a treatment instrument including an end effector capable of applying a high frequency current to a biological tissue and an electric element actuates the end effector.

DESCRIPTION OF THE RELATED ART

US Patent Application 2013/0190660A1 discloses a treatment system including a treatment instrument having an end effector and a counter electrode plate separate from the treatment instrument. In the treatment system, the treatment instrument includes an ultrasonic transducer as an electric element. In treatment using the treatment system, the end effector is brought into contact with a biological tissue as a treatment target in a state in which second electric energy is supplied to the ultrasonic transducer at the same time as first electric energy, i.e., high-frequency power, is supplied to the end effector and the counter electrode plate. Thus, a high frequency current flows through the treatment target between the end effector and the counter electrode plate. Heat caused by the high frequency current coagulates and/or incises the biological tissue. At this time, an ultrasonic vibration is generated in the ultrasonic transducer by the supply of the second electric energy, and the generated ultrasonic vibration is transmitted to the end effector. The end effector thereby vibrates, i.e., operates. The vibration of the end effector prevents the biological tissue from sticking to the end effector, i.e., burning, in a state in which the heat caused by the high frequency current is coagulating and/or incising the biological tissue.

In treatment using the treatment system as in US Patent Application 2013/0190660A1, the end effector is separated from the biological tissue after the heat caused by the high frequency current has coagulated and/or incised the biological tissue. When the end effector is separated from the biological tissue, as during the treatment of coagulating and/or incising the biological tissue, sticking of the biological tissue to the end effector is desired to be prevented.

BRIEF SUMMARY OF EMBODIMENTS

The disclosed technology has been made in view of the foregoing.

One aspect of the disclosed technology is directed to a treatment system comprises a power supply apparatus and a treatment instrument configured to communicate electrically with the power supply apparatus so as to perform a treatment on a biological tissue. The treatment instrument includes an end effector that transmits a high-frequency current delivered by a first electrical energy to the biological tissue. An electric element is configured to operate the end effector by being actuated using second electric energy. The power supply apparatus includes a processor configured to receive a stop command to cutoff the supply of the first electric energy and the second electric energy in a state in which the first electric energy and the second electric energy are supplied and determine whether or not the end effector is in contact with the biological tissue based on a parameter related to the first electric energy after receiving the stop command.

Another aspect of the disclosed technology is directed to a method of operating a treatment system in conjunction with a treatment instrument including an end effector configured to apply a high frequency current to a biological tissue delivered by a first electric energy and an electric element configured to operate the end effector by generating ultrasonic vibration delivered by a second electrical energy. The method comprises receiving a stop command to cutoff the supply of the first electric energy and the second electric energy in a state in which the first electric energy and the second electric energy are supplied and determining whether or not the end effector is in contact with the biological tissue based on a parameter related to the first electric energy after receiving the stop command.

A further aspect of the disclosed technology is directed to a method of operating a treatment instrument of comprises an end effector applying a high frequency current to a biological tissue, the end effector applying an ultrasonic vibration to the biological tissue by transmitting the ultrasonic vibration; and in a state of treating the biological tissue by applying the high frequency current and the ultrasonic vibration to the biological tissue, applying the ultrasonic vibration to the biological tissue and detecting whether or not the end effector is in contact with the biological tissue after completion of treatment of the biological tissue, and stopping the ultrasonic vibration when determining that the end effector is not in the contact.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

It is an object of the disclosed technology to provide a control device that effectively prevents sticking of a biological tissue to an end effector when the end effector after application of a high frequency current is separated from the biological tissue in a treatment system that can feed the high frequency current through the biological tissue.

First Embodiment

A first embodiment of the disclosed technology will be described with reference to FIGS. 1 to 7.

Figure 1:
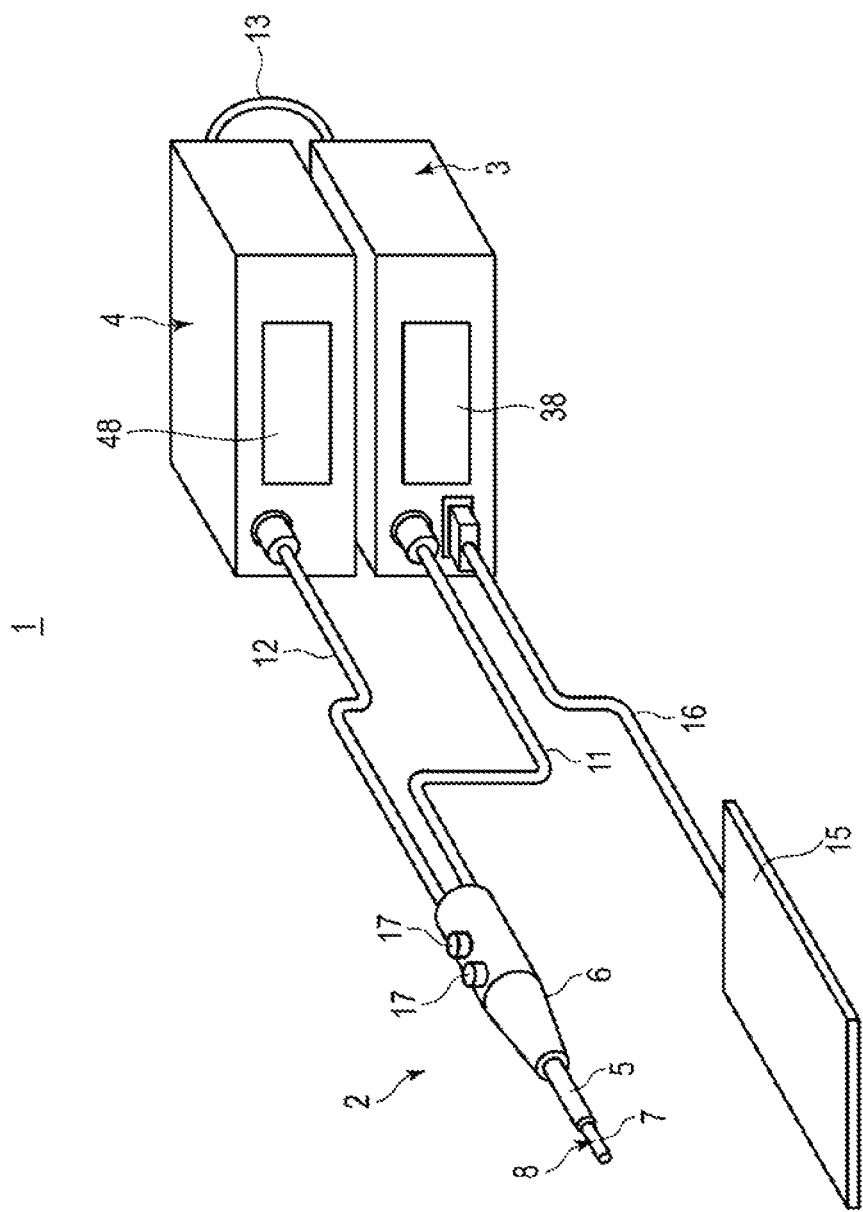
FIG. 1 is a schematic diagram depicting a treatment system according to a first embodiment.

FIG. 1 is a diagram depicting a treatment system 1 according to the present embodiment. As depicted in FIG. 1, the treatment system 1 includes a treatment instrument 2 and power supply devices 3 and 4. The treatment instrument 2 includes a tubular shaft 5, a housing 6, and an end effector 7. The housing 6 is coupled to one side of the shaft 5 in a direction along a central axis of the shaft 5. In addition, the housing 6 can be held by an operator or the like. In the present embodiment, the central axis of the housing 6 is coaxial with or substantially coaxial with the central axis of the shaft 5. Here, a side on which the housing 6 is located with respect to the shaft 5 in the direction along the central axis of the shaft 5 is set as a proximal end side, and an opposite side from the proximal end side is set as a distal end side.

In the treatment instrument 2, a rod member 8 is passed through the inside of the shaft 5 from the inside of the housing 6, and is extended toward the distal end side. The rod member 8 is projected to the distal end side from the distal end of the shaft 5. The end effector 7 is formed by a part of the rod member 8 which partially projected from the shaft 5. In the present embodiment, the rod member 8 is formed of a material having high vibration transmissibility such as a titanium alloy. In addition, the end effector 7 has conductivity.

The housing 6 is detachably connected to the power supply device 3, i.e., a first power supply device, via a cable 11, and is detachably connected to the power supply device 4, i.e., a second power supply device, via a cable 12. In addition, the power supply devices 3 and 4 are connected to each other via a cable 13. Incidentally, in a certain example, the power supply devices 3 and 4 may be capable of wireless communication with each other instead of having the cable 13. In addition, the treatment system 1 has a counter electrode plate 15 having conductivity. The counter electrode plate 15 is detachably connected to the power supply device 3 via a cable 16.

The housing 6 has operating buttons 17 (two operating buttons in the present embodiment) as operating members. Each of the operating buttons 17 allows input of an operation of simultaneously supplying first electric energy and second electric energy to the treatment instrument 2. Incidentally, in a certain example, in place of the operating buttons 17 or in addition to the operating buttons 17, a foot switch or the like separate from the treatment instrument 2 may be disposed as an operating member that allows input of an operation of simultaneously supplying the first electric energy and the second electric energy to the treatment instrument 2.

Figure 2:
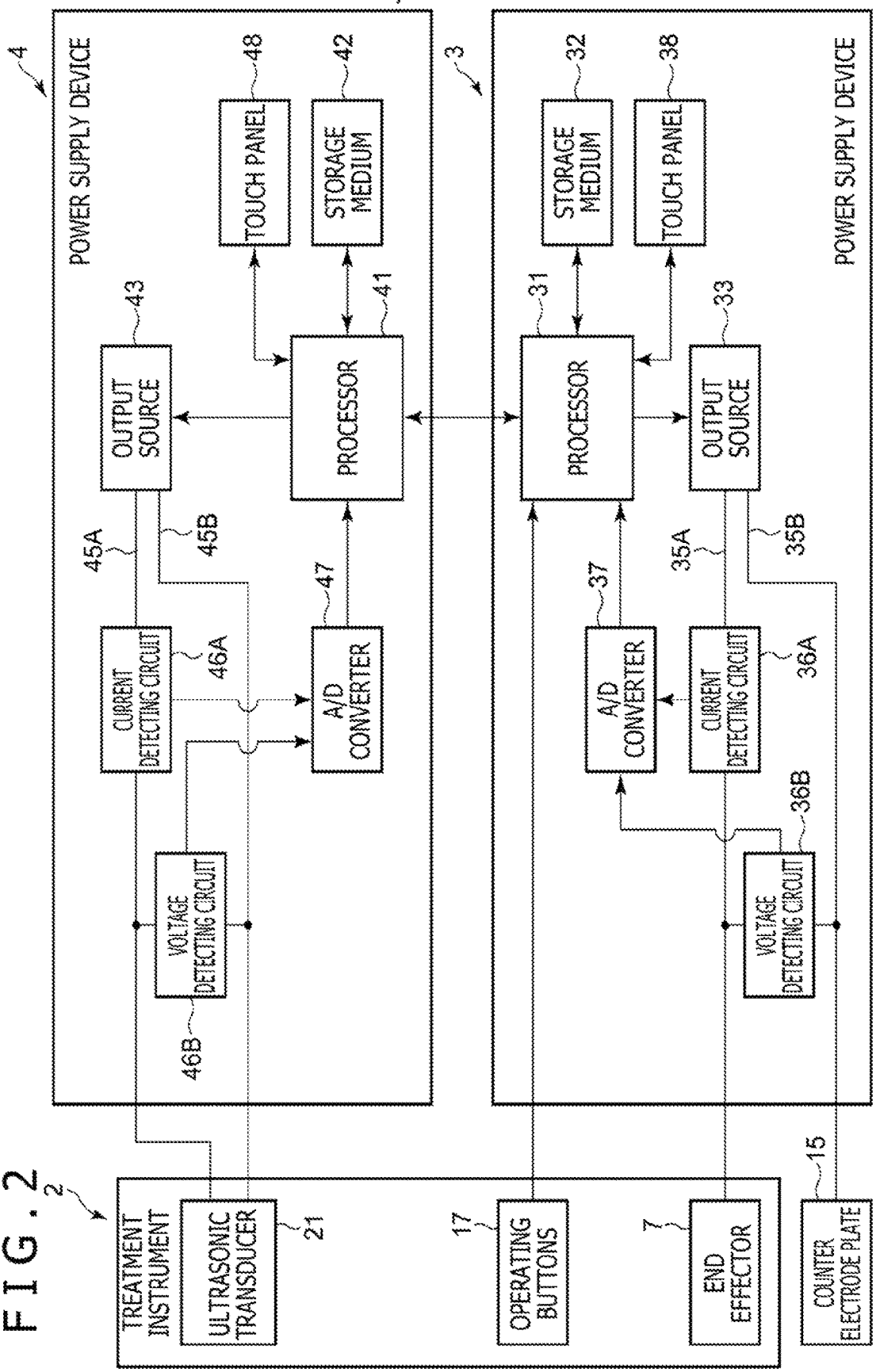
FIG. 2 is a block diagram schematically depicting a configuration that supplies first electric energy and second electric energy to a treatment instrument according to the first embodiment.

FIG. 2 is a diagram depicting a configuration that supplies the first electric energy and the second electric energy to the treatment instrument 2. As depicted in FIG. 2, the power supply device 3 includes a processor 31, i.e., a controller, and a storage medium 32, and the power supply device 4 includes a processor 41, i.e., a controller, and a storage medium 42. Each of the processors 31 and 41 is formed by an integrated circuit including a CPU (Central Processing Unit), an ASIC (Application Specific Integrated Circuit), an FPGA (Field Programmable Gate Array), or the like. Only one processor 31 may be arranged in the power supply device 3, or a plurality of processors 31 may be arranged in the power supply device 3. Similarly, only one processor 41 may be arranged in the power supply device 4, or a plurality of processors 41 may be arranged in the power supply device 4. In the present embodiment, each of the processors 31 and 41 constitutes at least a part of a control device that controls the treatment system 1.

Processing in the processor 31 is performed according to a program stored in the processor 31 or the storage medium 32. The storage medium 32 stores the processing program used by the processor 31 and a parameter, a function, a table, and the like used for operation in the processor 31. Similarly, processing in the processor 41 is performed according to a program stored in the processor 41 or the storage medium 42. The storage medium 42 stores the processing program used by the processor 41 and a parameter, a function, a table, and the like used for operation in the processor 41. In addition, the processors 31 and 41 can exchange information with each other by wire or by radio.

The processors 31 and 41 determine whether operating input is being performed at each of the operating buttons 17, i.e., operating members, that is, whether operating input at each of the operating buttons 17 is ON or OFF. In a certain example, switches (not depicted) are arranged within the housing 6 so as to correspond to the respective operating buttons 17, and each of the switches between ON and OFF in correspondence with an operation at the corresponding operating button (corresponding one of the operating buttons 17). The processors 31 and 41 detect whether the respective switches are ON or OFF. Then, the processors 31 and 41 determine whether or not operating input is being performed at the respective operating buttons 17 based on detection results with regard to the corresponding switches.

The processors 31 and 41 determine that a detection signal indicating a switching from a state in which operating input is not performed at any of the operating buttons 17 to a state in which operating input is being performed at only one of the operating buttons 17 is a supply start command to start simultaneous supply of the first electric energy and the second electric energy to the treatment instrument 2. Therefore, the processors 31 and 41 receive the supply start command when a switching is made from the state in which operating input at all of the operating buttons 17 is OFF to the state in which operating input at only one of the operating buttons 17 is ON. In addition, the processors 31 and 41 determine that a detection signal indicating a switching from the state in which operating input is being performed at only one of the operating buttons 17 to the state in which operating input is not performed at any of the operating buttons 17 is a stop command to stop the supply of the first electric energy and the second electric energy to the treatment instrument 2. Therefore, the processors 31 and 41 receive the stop command when a switching is made from the state in which operating input at only one of the operating buttons 17 is ON to the state in which operating input at all of the operating buttons 17 is OFF.

The power supply device 3 includes an output source 33, i.e., a high-frequency power supply. The output source 33 includes a waveform generator, a converting circuit, a relay circuit, a transformer, and the like, and forms a driving circuit, i.e., a high frequency driving circuit. The output source 33 can convert power from a battery power supply, an outlet power supply, or the like into high-frequency power as the first electric energy, and output the first electric energy. The output source 33 is electrically connected to the end effector 7 via an electric path 35A, and is electrically connected to the counter electrode plate 15 via an electric path 35B. The electric path 35A is, for example, extended through the interior of the cable 11. The electric path 35B is, for example, extended through the interior of the cable 16.

The first electric energy output from the output source 33 is supplied to the end effector 7 and the counter electrode plate 15 via the electric paths 35A and 35B. When the first electric energy, i.e., high-frequency power, is supplied to the end effector 7 and the counter electrode plate 15, the end effector 7 and the counter electrode plate 15 function as electrodes having potentials different from each other. It is thereby possible to feed a high frequency current through a biological tissue or the like between the end effector 7 and the counter electrode plate 15, and to thus apply the high frequency current to the biological tissue or the like. Based on operation at each of the operating buttons 17 or the like, the processor 31 controls output from the output source 33, and thereby controls the supply of the first electric energy to the end effector 7 and the counter electrode plate 15.

In addition, the power supply device 3 includes a current detecting circuit 36A, a voltage detecting circuit 36B, and an A/D converter 37. The current detecting circuit 36A detects an output current I from the output source 33 to the end effector 7 and the counter electrode plate 15. The voltage detecting circuit 36B detects an output voltage V to the end effector 7 and the counter electrode plate 15. The A/D converter 37 converts an analog signal indicating the current value of the output current I detected by the current detecting circuit 36A and an analog signal indicating the voltage value of the output voltage V detected by the voltage detecting circuit 36B into digital signals. The A/D converter 37 transmits the converted digital signals to the processor 31. Thus, the processor 31 obtains information regarding the output current I and the output voltage V from the output source 33, and calculates the output current I and the output voltage V from the output source 33 as parameters related to the first electric energy.

In addition, based on a result of the calculation of the output current I and the output voltage V from the output source 33 or the like, the processor 31 calculates impedance Z of a circuit through which the output current I flows and output power P from the output source 33 or the like as parameters related to the first electric energy. Based on the parameters related to the first electric energy including the output current I, the output voltage V, the impedance Z, and the output power P or the like, the processor 31 controls the output of the first electric energy from the output source 33 to the end effector 7 and the counter electrode plate 15.

In addition, in the present embodiment, the power supply device 3 has a touch panel 38. The touch panel 38 functions, for example, as an input unit to which a setting with regard to output from the output source 33 such as an output level from the output source 33 can be input. In addition, the touch panel 38 also functions, for example, as a display unit displaying information regarding output from the output source 33 such as the output current I and the output voltage V from the output source 33.

The treatment instrument 2 includes an ultrasonic transducer 21 as an electric element. The ultrasonic transducer 21 is connected to the rod member 8 from the proximal end side within the housing 6. In addition, the power supply device 4 includes an output source 43, i.e., an ultrasonic power supply. The output source 43 includes a waveform generator, a converting circuit, a relay circuit, a transformer, and the like, and forms a driving circuit, i.e., an ultrasonic driving circuit. The output source 43 can convert power from a battery power supply, an outlet power supply, or the like into the second electric energy, and output the second electric energy. The output source 43 is connected to the ultrasonic transducer 21 via electric paths 45A and 45B.

Each of the electric paths 45A and 45B is, for example, extended through the interior of the cable 12. The second electric energy output from the output source 43 is supplied to the ultrasonic transducer 21 via the electric paths 45A and 45B. At this time, alternating-current power having a certain frequency in a predetermined frequency range is supplied as the second electric energy to the ultrasonic transducer 21. Based on operation at each of the operating buttons 17 or the like, the processor 41 controls output from the output source 43, and thereby controls the supply of the second electric energy to the ultrasonic transducer 21.

When the second electric energy, i.e., alternating-current power, is supplied to the ultrasonic transducer 21, the ultrasonic transducer 21 is actuated, and an ultrasonic vibration is generated in the ultrasonic transducer 21. The generated ultrasonic vibration is transmitted to the end effector 7 via the rod member 8. The end effector 7 vibrates when the ultrasonic vibration is transmitted to the end effector 7. In other words, the end effector 7 is operated by actuating the ultrasonic transducer 21 as an electric element. At this time, the rod member 8 including the end effector 7 vibrates at a certain frequency in a predetermined frequency range. In the present embodiment, a vibration direction of the rod member 8 is parallel or substantially parallel with a longitudinal axis C.

In addition, the power supply device 4 includes a current detecting circuit 46A, a voltage detecting circuit 46B, and an A/D converter 47. The current detecting circuit 46A detects an output current I' from the output source 43 to the ultrasonic transducer 21. The voltage detecting circuit 46B detects an output voltage V' to the ultrasonic transducer 21. The A/D converter 47 converts an analog signal indicating the current value of the output current I' detected by the current detecting circuit 46A and an analog signal indicating the voltage value of the output voltage V' detected by the voltage detecting circuit 46B into digital signals. The A/D converter 47 transmits the converted digital signals to the processor 41. Thus, the processor 41 obtains information regarding the output current I' and the output voltage V' from the output source 43, and calculates the output current I' and the output voltage V' from the output source 43 as parameters related to the second electric energy.

In addition, based on a result of the calculation of the output current I' and the output voltage V' from the output source 43 or the like, the processor 41 calculates impedance Z' of the ultrasonic transducer 21, or the impedance of a circuit through which the output current I' flows, and output power P' from the output source 43 or the like, as parameters related to the second electric energy. Based on the parameters related to the second electric energy including the output current I', the output voltage V', the impedance Z', and the output power P' or the like, the processor 41 controls the output of the second electric energy from the output source 43 to the ultrasonic transducer 21. In a certain example, the processor 41 performs PLL control (Phase Lock Loop control) into a state with no phase difference between the output current I' and the output voltage V'. In addition, in the present embodiment, the processor 41 obtains, from the processor 31, parameters related to the first electric energy including the output current I, the output voltage V, the impedance Z, and the output power P or the like. Then, the processor 41 controls the output of the second electric energy to the ultrasonic transducer 21 based on the parameters related to the first electric energy in addition to the parameters related to the second electric energy.

In addition, in the present embodiment, the power supply device 4 has a touch panel 48. The touch panel 48 functions, for example, as an input unit to which a setting related to output from the output source 43 such as an output level from the output source 43 can be input. In addition, the touch panel 48 also functions, for example, as a display unit displaying information regarding output from the output source 43 such as the output current I' and the output voltage V' from the output source 43.

Description will next be made of the action and effect of the control device formed by the processors 31 and 41 and the treatment system 1 according to the present embodiment. When an operator is to perform treatment using the treatment system 1, the operator places the counter electrode plate 15 on a subject such as a human body, and holds the housing 6. Then, the end effector 7 is disposed in the vicinity of a biological tissue to be treated, and operating input is performed at one of the operating buttons 17. When operating input at one of the operating buttons 17 is ON, the processor 31 supplies the first electric energy to the end effector 7 and the counter electrode plate 15, and the processor 41 supplies the second electric energy to the ultrasonic transducer 21. Then, the end effector 7 is brought into contact with the biological tissue to be treated in a state in which both the first electric energy and the second electric energy are supplied to the treatment instrument 2.

When the end effector 7 comes into contact with the biological tissue in a state in which the first electric energy is supplied to the treatment instrument 2, a high frequency current flows through the biological tissue between the end effector 7 and the counter electrode plate 15, and thus the high frequency current is applied to the biological tissue. Heat caused by the high frequency current alters the biological tissue, and coagulates and/or incises the biological tissue to be treated. Here, in a case where operating input is performed at certain one of the operating buttons 17, the processor 31 controls the output of the first electric energy from the output source 33 in a first treatment mode. In this case, a high frequency current of a continuous waveform is output as the output current I from the output source 33, and the heat caused by the high frequency current mainly incises the biological tissue. When operating input is performed at another certain one of the operating buttons 17, on the other hand, the processor 31 controls the output of the first electric energy from the output source 33 in a second treatment mode different from the first treatment mode. In this case, a high frequency current of a burst waveform (interrupted waveform) is output as the output current I from the output source 33, and the heat caused by the high frequency current mainly coagulates (seals) the biological tissue.

In addition, the ultrasonic transducer 21 is actuated when operating input at one of the operating buttons 17 is ON, and the second electric energy is supplied to the ultrasonic transducer 21. Thus, a vibration generated by the ultrasonic transducer 21 is transmitted to the end effector 7, and the end effector 7 vibrates, i.e., operates. The vibration of the end effector 7 prevents the biological tissue from sticking to the end effector 7, i.e., burning, in a state in which the heat caused by the high frequency current is coagulating and/or incising the biological tissue.

Then, after coagulating and/or incising the biological tissue by the high frequency current as described hereinbefore, the operator stops the operating input at the operating button at which the operating input is being performed (corresponding one of the operating buttons 17). Then, the operator separates the end effector 7 from the biological tissue after stopping the operating input at the operating button at which the operating input is being performed (corresponding one of the operating buttons 17), that is, after switching, to OFF, the operating input at the operating button at which the operating input is being performed (corresponding one of the operating buttons 17). Incidentally, the operating input at the operating button at which the operating input is being performed (corresponding one of the operating buttons 17) may be stopped after the end effector 7 is separated from the biological tissue after the biological tissue is coagulated and/or incised.

Figure 3:
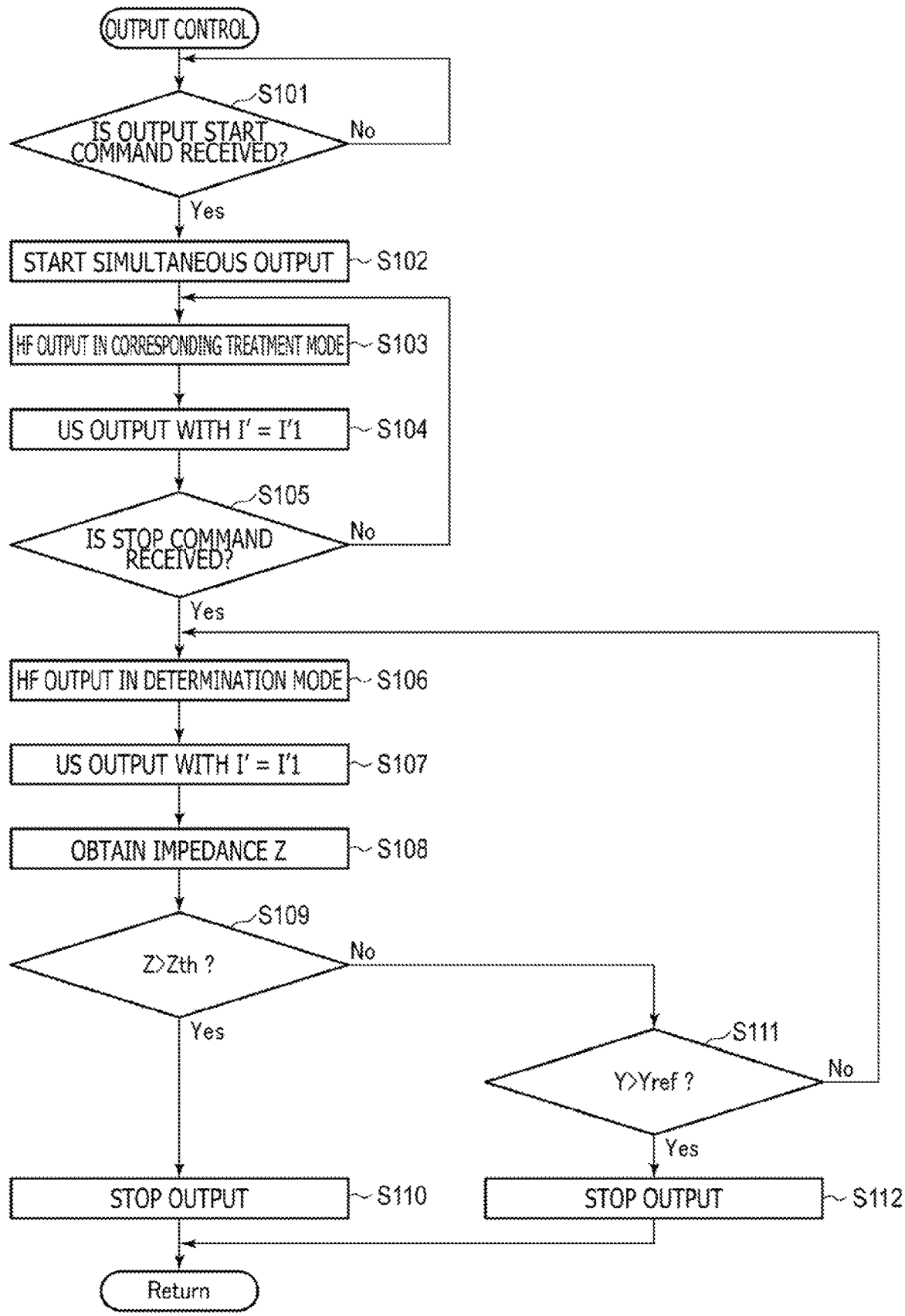
FIG. 3 is a flowchart depicting processing in output control of the first electric energy and the second electric energy, the processing being performed by processors according to the first embodiment.

FIG. 3 is a flowchart depicting processing performed by the processors 31 and 41 in output control of the first electric energy and the second electric energy. As depicted in FIG. 3, in the output control of the first electric energy and the second electric energy, the processors 31 and 41 determine whether or not a supply start command is received, in S101. In the present embodiment, as described hereinbefore, the processors 31 and 41 receive the supply start command when a switching is made from a state in which operating input at all of the operating buttons 17 is stopped to a state in which operating input is being performed at only one of the operating buttons 17. When the supply start command is not received (S101—No), the processing returns to S101. Hence, the processors 31 and 41 wait until receiving the supply start command. When the supply start command is received (S101—Yes), the processor 31 starts the output of the first electric energy from the output source 33, and the processor 41 starts the output of the second electric energy from the output source 43. In other words, the processors 31 and 41 start simultaneous output of the first electric energy and the second electric energy in S102.

When the simultaneous output of the first electric energy and the second electric energy is started, the processor 31 outputs the first electric energy in a treatment mode corresponding to the operating button (corresponding one of the operating buttons 17) at which the operating input is being performed (the first treatment mode or the second treatment mode described hereinbefore), in S103. At this time, in either treatment mode, that is, irrespective of the operating button (corresponding one of the operating buttons 17) at which the operating input is being performed among the operating buttons 17, the processor 31 adjusts the output current I and the output voltage V from the output source 33 or the like to a state in which the heat caused by the high frequency current alters the biological tissue. In other words, in either treatment mode, the processor 31 controls the output of the first electric energy from the output source 33 to a state in which the high frequency current causes the biological tissue to be coagulated and/or incised.

In addition, when the simultaneous output of the first electric energy and the second electric energy is started, the processor 41 controls the output from the output source 43 by constant current control that holds the output current I' from the output source 43 constant or substantially constant at a current value I'1 with the passage of time, in S104. Here, amplitude of the ultrasonic transducer 21 and amplitude of the end effector 7 when a vibration is transmitted from the ultrasonic transducer 21 change so as to correspond to the output current I'. Therefore, the amplitude of the end effector 7 which amplitude is in accordance with the ultrasonic vibration is held constant or substantially constant with the passage of time by performing the constant current control described hereinbefore on the output current I'.

The processors 31 and 41 then determine whether or not a stop command is received, in S105. In the present embodiment, as described hereinbefore, the processors 31 and 41 receive the stop command when a switching is made from a state in which operating input is being performed at only one of the operating buttons 17 to a state in which operating input is not performed at any of the operating buttons 17. When the stop command is not received (S105—No), the processing returns to S103, and the processors 31 and 41 sequentially perform the processing from S103 on down. Hence, until the processors 31 and 41 receive the stop command, the processors 31 and 41 continue performing the output control of the first electric energy in the corresponding treatment mode in S103 and the constant current control described hereinbefore on the output of the second electric energy in S104.

When the processor 31 receives the stop command (S105—Yes), the processor 31 switches the output of the first electric energy to a determination mode, and outputs the first electric energy from the output source 33 in the determination mode, in S106. When a switching is made to the determination mode, the output of the first electric energy to the end effector 7 and the counter electrode plate 15, that is, HF output, is decreased as compared with the treatment mode. Hence, based on the reception of the stop command, the processor 31 decreases the output of the first electric energy as compared with the output of the first electric energy before the reception of the stop command. Because the output of the first electric energy is decreased, the output current I, the output voltage V, and the output power P or the like from the output source 33 are decreased in the determination mode as compared with the treatment mode. In the determination mode, the processor 31 decreases the output of the first electric energy from the output source 33 to a degree that the high frequency current does not cause the biological tissue to be altered. However, also in the determination mode, the end effector 7 is in contact with the biological tissue, and thus, the high frequency current, though minute, flows through the biological tissue between the end effector 7 and the counter electrode plate 15.

In the present embodiment, also after receiving the stop command, the processor 41 controls the output from the output source 43 by the constant current control that holds the output current I' from the output source 43 constant or substantially constant at the current value I'1 with the passage of time, in S107. Therefore, also after the stop command is received, the supply of the second electric energy to the ultrasonic transducer 21 is continued, and the end effector 7 continues vibrating, i.e., operating. In addition, when receiving the stop command (S105—Yes), the processor 31 obtains the impedance Z of the circuit through which the output current I flows, based on the output current I and the output voltage V from the output source 33, in S108.

The processors 31 and 41 then determine whether or not the obtained impedance Z is higher than a threshold value Zth, in S109. In other words, the determination is performed based on the parameter related to the first electric energy after a point in time at which the output from the output source 33 is decreased. Here, the impedance Z changes so as to correspond to whether or not the end effector 7 is in contact with the biological tissue. When the end effector 7 is in contact with the biological tissue, the high frequency current flows easily between the end effector 7 and the counter electrode plate 15, and the impedance Z is low. When the end effector 7 is not in contact with the biological tissue, on the other hand, the high frequency current does not flow or does not flow easily between the end effector 7 and the counter electrode plate 15, and the impedance Z is high. Therefore, whether or not the end effector 7 is in contact with the biological tissue is determined appropriately based on whether or not the impedance Z is higher than the threshold value Zth.

When the impedance Z is higher than the threshold value Zth (S109—Yes), the processors 31 and 41 determine that the end effector 7 is separated from the biological tissue, and stop the output of the first electric energy from the output source 33 and the output of the second electric energy from the output source 43 in S110. The supply of the first electric energy to the end effector 7 and the counter electrode plate 15 and the supply of the second electric energy to the ultrasonic transducer 21 are thereby stopped.

When the impedance Z is equal to or lower than the threshold value Zth (S109—No), the processors 31 and 41 determine that the end effector 7 is in contact with the biological tissue. The processors 31 and 41 then determine whether or not an elapsed time Y from a point in time at which the stop command is received is longer than a reference time Yref, in S111. When the elapsed time Y is longer than the reference time Yref (S111—Yes), the processors 31 and 41 determine that a problem or the like has occurred, and stop the output of the first electric energy from the output source 33 and the supply of the second electric energy from the output source 43, in S112.

On the other hand, when the elapsed time Y is equal to or less than the reference time Yref (S111—No), the processing returns to S106, and the processors 31 and 41 sequentially perform the processing from S106 on down. Hence, before the passage of the reference time Yref from the point in time at which the stop command is received, as long as the impedance Z is equal to or lower than the threshold value Zth, the processors 31 and 41 continue performing the output control of the first electric energy in the determination mode in S106 and the constant current control described hereinbefore on the output of the second electric energy in S107. Hence, as long as the elapsed time Y is equal to or less than the reference time Yref and the impedance Z is equal to or lower than the threshold value Zth, it is determined that the end effector 7 is in contact with the treatment target, so that the supply of the second electric energy to the ultrasonic transducer 21 is continued and the end effector 7 continues vibrating, i.e., operating.

Figure 4:
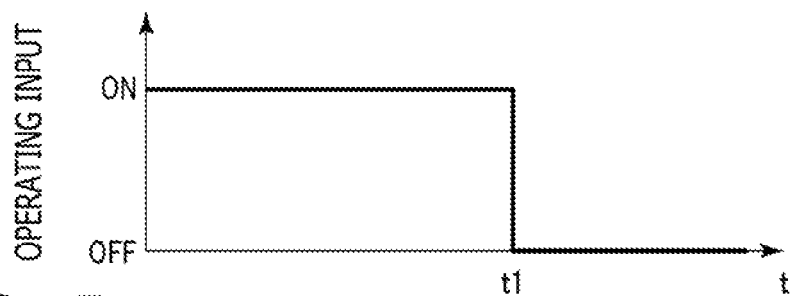
FIG. 4 is a schematic diagram depicting an example of switching between ON and OFF of operating input at one certain operating member with the passage of time in the first embodiment.
Figure 5:
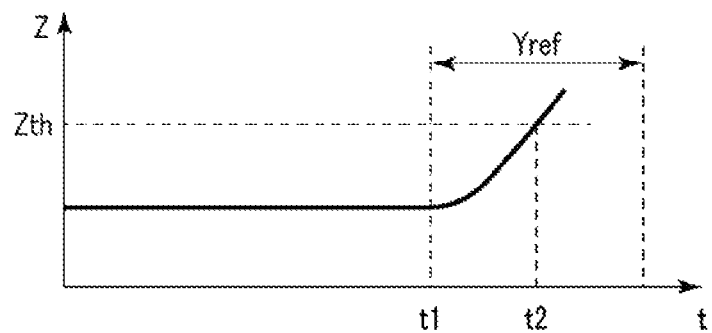
FIG. 5 is a schematic diagram depicting an example of changes in impedance with the passage of time in a case where the ON-OFF state of the operating input at the operating member changes as in FIG. 4 in the first embodiment.
Figure 6:
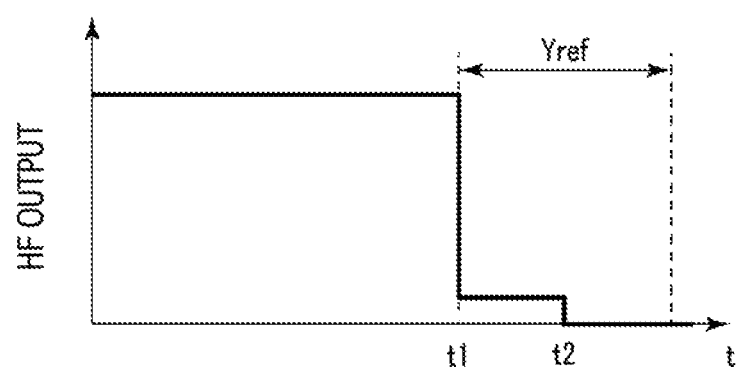
FIG. 6 is a schematic diagram depicting an example of changes in HF (high-frequency) output with the passage of time in a case where the ON-OFF state of the operating input at the operating member changes as in FIG. 4 and the impedance Z changes as in FIG. 5 in the first embodiment.
Figure 7:
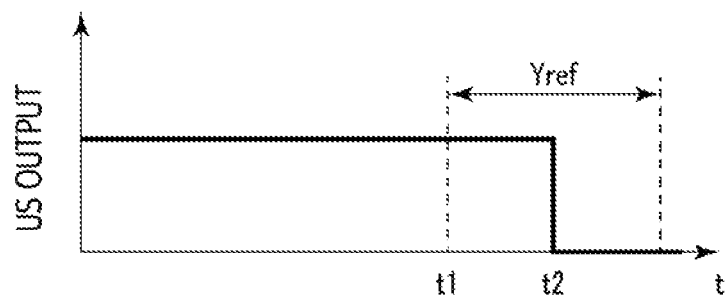
FIG. 7 is a schematic diagram depicting an example of changes in US (ultrasonic) output with the passage of time in a case where the ON-OFF state of the operating input at the operating member changes as in FIG. 4 and the impedance Z changes as in FIG. 5 in the first embodiment.

FIG. 4 depicts an example of switching between ON and OFF of operating input at one certain operating member (certain one of the operating buttons 17) with the passage of time. FIG. 5 depicts an example of changes in the impedance Z with the passage of time in a case where the ON-OFF state of the operating input at the operating member (certain one of the operating buttons 17) changes as in FIG. 4. FIG. 6 depicts an example of changes in HF output as the output of the first electric energy from the output source 33 with the passage of time in a case where the ON-OFF state of the operating input at the operating member (certain one of the operating buttons 17) changes as in FIG. 4 and the impedance Z changes as in FIG. 5. FIG. 7 depicts an example of changes in US output as the output of the second electric energy from the output source 43 with the passage of time in a case where the ON-OFF state of the operating input at the operating member (certain one of the operating buttons 17) changes as in FIG. 4 and the impedance Z changes as in FIG. 5. In FIGS. 4 to 7, an axis of abscissas indicates, for example, time t as a reference for a start of the simultaneous output of the first electric energy and the second electric energy. In addition, in FIG. 4, an axis of ordinates indicates the ON-OFF state of the operating input at the operating member (certain one of the operating buttons 17). In FIG. 5, an axis of ordinates indicates the impedance Z. In FIG. 6, an axis of ordinates indicates a level of the HF output. In FIG. 7, an axis of ordinates indicates a level of the US output.

In an example of FIGS. 4 to 7, at time t1, the operating input at the operating member (certain one of the operating buttons 17) is stopped, and thus, the operating input at the operating member (certain one of the operating buttons 17) is switched to OFF. Therefore, the processors 31 and 41 receive the stop command at time t1 or immediately after time t1. Then, as depicted in FIG. 6, at time t1 or immediately after time t1, the processor 31 switches the output of the first electric energy to the determination mode by the processing of S106. Thus, after the change to the determination mode, the output of the first electric energy is decreased as compared with the output of the first electric energy before time t1. In addition, as depicted in FIG. 7, also after time t1, the supply of the second electric energy to the ultrasonic transducer 21 is continued, and the end effector 7 continues vibrating.

In addition, in the example of FIGS. 4 to 7, after stopping the operating input at the operating member (certain one of the operating buttons 17) at time t1, the operator separates the end effector 7 from the biological tissue. When a movement of separating the end effector 7 from the biological tissue is started, the impedance Z increases with the passage of time. In the example of FIGS. 4 to 7, the end effector 7 is completely out of contact with the biological tissue at time t2 before the passage of the reference time Yref from time t1 or near time t2. Therefore, as depicted in FIG. 5, at time t2, the impedance Z reaches the threshold value Zth. Immediately after time t2, the impedance Z increases to a value higher than the threshold value Zth. Incidentally, the impedance Z is, for example, infinite, in a state in which the end effector 7 is completely out of contact with the biological tissue. Then, at time t2 or immediately after time t2, the processors 31 and 41 determine that the impedance Z has become higher than the threshold value Zth, and therefore determine that the end effector 7 is not in contact with the biological tissue. Thus, as depicted in FIG. 6 and FIG. 7, at time t2 or immediately after time t2, the processors 31 and 41 stop the output of the first electric energy and the output of the second electric energy by the processing of S110.

As described hereinbefore, in the present embodiment, even when the processors 31 and 41 receive the stop command, the processors 31 and 41 continue the supply of the second electric energy, and thereby continue vibrating, i.e., operating, the end effector 7, as long as the processors 31 and 41 determine that the end effector 7 is in contact with the biological tissue. Therefore, even when the end effector 7 is in contact with the biological tissue after the processors 31 and 41 receive the stop command, sticking of the biological tissue to the end effector 7 is prevented effectively.

In addition, in the present embodiment, based on the determination that the end effector 7 is not in contact with the biological tissue after the stop command is received, the processors 31 and 41 stop the output of the first electric energy and the output of the second electric energy. Therefore, in a state in which the end effector 7 is completely separated from the biological tissue after the stop command is received, the supply of the second electric energy to the ultrasonic transducer 21, i.e., an electric element, is stopped, and the vibration, i.e., operation, of the end effector 7 is stopped. In other words, while the end effector 7 is being separated from the biological tissue after the stop command is received, the ultrasonic transducer 21 is operated, and the end effector 7 vibrates. Therefore, when the end effector 7 is separated from the biological tissue, sticking of the biological tissue to the end effector 7 is prevented effectively.

In addition, in the present embodiment, also after the stop command is received, the first electric energy is output from the output source 33 to a degree that the high frequency current does not cause the biological tissue to be altered. Therefore, also after receiving the stop command, the processor 31 can obtain the impedance Z of the circuit through which the output current I flows. Then, also after receiving the stop command, the processors 31 and 41 can appropriately determine whether or not the end effector 7 is in contact with the biological tissue based on the impedance Z.

Modifications

Incidentally, in the first embodiment, whether or not the end effector 7 is in contact with the biological tissue is determined based on the impedance Z. However, there is no limitation to this. In a certain modification, the output current I from the output source 33 as one parameter related to the first electric energy is used in place of the impedance Z to determine whether or not the end effector 7 is in contact with the biological tissue. In the present modification, when the processor 31 receives the stop command (S105—Yes), the processor 31 obtains the output current I (current value of the output current I) from the output source 33, in place of the processing of S108. Then, the processors 31 and 41 determine whether or not the obtained output current I is larger than a threshold value Ith, in place of the processing of S109. When the end effector 7 is in contact with the biological tissue, the high frequency current flows easily between the end effector 7 and the counter electrode plate 15, and the output current I is large. When the end effector 7 is not in contact with the biological tissue, on the other hand, the high frequency current does not flow or does not flow easily between the end effector 7 and the counter electrode plate 15, and the output current I is small. Hence, whether or not the end effector 7 is in contact with the biological tissue is determined appropriately based on whether or not the output current I is larger than the threshold value Ith.

In the present modification, when the output current I is equal to or less than the threshold value Ith, the processors 31 and 41 determine that the end effector 7 is separated from the biological tissue, and stop the output of the first electric energy and the output of the second electric energy as in the processing of S5110. When the output current I is larger than the threshold value Ith, on the other hand, the processors 31 and 41 determine that the end effector 7 is in contact with the biological tissue. Then, when the elapsed time Y is equal to or less than the reference time Yref in S111 (S111—No), the processing returns to S106. Hence, in the present modification, as long as the elapsed time Y is equal to or less than the reference time Yref and the output current I is larger than the threshold value Ith, it is determined that the end effector 7 is in contact with the treatment target, so that the supply of the second electric energy to the ultrasonic transducer 21 is continued and the end effector 7 continues vibrating, i.e., operating.

In addition, in another certain modification, the output power P from the output source 33 as one parameter related to the first electric energy is used to determine whether or not the end effector 7 is in contact with the biological tissue. In the present modification, when the processor 31 receives the stop command (S105—Yes), the processor 31 obtains the output power P from the output source 33, in place of the processing of S108. Then, the processors 31 and 41 determine whether or not the obtained output power P is higher than a threshold value Pth, in place of the processing of S109. When the end effector 7 is in contact with the biological tissue, the output current I is large, and therefore, the output power P is also high. When the end effector 7 is not in contact with the biological tissue, on the other hand, the output current I is small, and therefore, the output power P is also low. Hence, whether or not the end effector 7 is in contact with the biological tissue is determined appropriately based on whether or not the output power P is higher than the threshold value Pth.

In the present modification, when the output power P is equal to or lower than the threshold value Pth, the processors 31 and 41 determine that the end effector 7 is separated from the biological tissue, and stop the output of the first electric energy and the output of the second electric energy as in the processing of S110. When the output power P is higher than the threshold value Pth, on the other hand, the processors 31 and 41 determine that the end effector 7 is in contact with the biological tissue. Then, when the elapsed time Y is equal to or less than the reference time Yref in S111 (S111—No), the processing returns to S106. Hence, in the present modification, as long as the elapsed time Y is equal to or less than the reference time Yref and the output power P is higher than the threshold value Pth, it is determined that the end effector 7 is in contact with the treatment target, so that the supply of the second electric energy to the ultrasonic transducer 21 is continued and the end effector 7 continues vibrating, i.e., operating.

Figure 8:
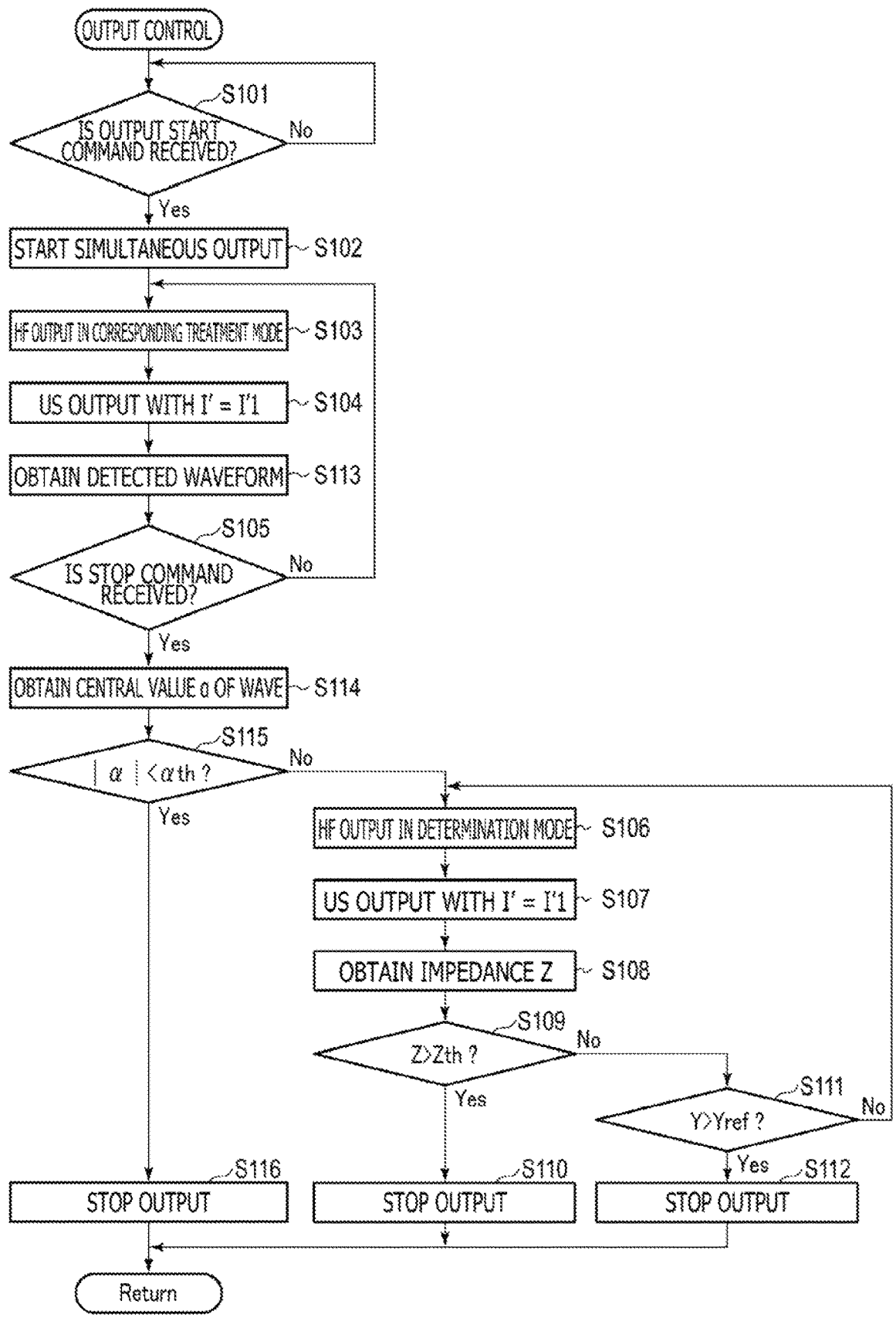
FIG. 8 is a flowchart depicting processing in the output control of the first electric energy and the second electric energy, the processing being performed by processors according to a first modification.

In addition, in a first modification depicted in FIG. 8, whether or not the end effector 7 is in contact with the biological tissue is determined based on a parameter related to the first electric energy at a point in time at which the processors 31 and 41 receive the stop command or immediately before the point in time at which the processors 31 and 41 receive the stop command. Also in the present modification, as in the first embodiment, the processors 31 and 41 perform the processing of S101 to S105. However, in the present modification, when the simultaneous output of the first electric energy and the second electric energy is started (S102—Yes), the processor 31 obtains a detected waveform of the output current I detected by the current detecting circuit 36A or a detected waveform of the output voltage V detected by the voltage detecting circuit 36B, in S113. Then, the processor 31 continues the obtainment of the detected waveform in S113 while the output control of the first electric energy in the corresponding treatment mode in S103 and the constant current control described hereinbefore on the output of the second electric energy in S104 are performed, that is, until the processor 31 receives the stop command.

Then, in the present modification, when the processor 31 receives the stop command (S105—Yes), the processor 31 obtains a wave central value α, to be described hereinafter, of the detected waveform at a point in time at which the processor 31 receives the stop command or immediately before the point in time, in S114. In other words, the central value α of the detected waveform detected by the current detecting circuit 36A or the voltage detecting circuit 36B at the point in time at which the stop command is received or immediately before the point in time is obtained as a parameter related to the first electric energy. Then, the processors 31 and 41 determine whether or not an absolute value |α| of the obtained central value α of the detected waveform is smaller than a threshold value αth, in S115. When the absolute value |α| of the central value α is smaller than the threshold value αth (S115—Yes), the processors 31 and 41 determine that the end effector 7 is not in contact with the biological tissue (treatment target), and stop the output of the first electric energy and the output of the second electric energy in S116.

When the absolute value |α| of the central value α is equal to or more than the threshold value αth (S115—No), on the other hand, the processors 31 and 41 determine that the end effector 7 is in contact with the biological tissue, i.e., treatment target, and the processing proceeds to S106. Then, as in the first embodiment, the processors 31 and 41 perform the processing of S106 to S112. Hence, in the present modification, when it is determined that the end effector 7 is in contact with the biological tissue based on the central value α of the detected waveform at the point in time at which the stop command is received or immediately before the point in time, the processor 31 switches to the output of the first electric energy in the determination mode and decreases the output of the first electric energy after the point in time at which the stop command is received. Then, after the output of the first electric energy is decreased, whether or not the end effector 7 is in contact with the biological tissue is determined as in the first embodiment or the like.

Here, in a state in which the heat caused by the high frequency current coagulates and/or incises the biological tissue and ultrasonic vibration vibrates, i.e., operates, the end effector 7, the end effector 7 repeats contacting the biological tissue and separating from the biological tissue at high speed. At this time, a space between the end effector 7 and the biological tissue is minute even in a state in which the end effector 7 is separated from the biological tissue. A discharge occurs at the end effector 7 when the first electric energy is output to the end effector 7 and the counter electrode plate 15 with high power, as in the output in the treatment mode or the like, in the state in which the end effector 7 repeats contacting the biological tissue and separating from the biological tissue at high speed. On the other hand, in a case where the end effector 7 is located so as to be separated from the biological tissue to a degree that the end effector 7 cannot contact the biological tissue, no discharge occurs at the end effector 7 even when the first electric energy is output to the end effector 7 and the counter electrode plate 15 with high power and ultrasonic vibration vibrates the end effector 7. Therefore, whether or not the end effector 7 is in contact with the biological tissue, that is, whether or not the end effector 7 is repeating contacting the biological tissue and separating from the biological tissue at high speed, is determined appropriately based on whether or not a discharge has occurred at the point in time at which the stop command is received or immediately before the point in time.

Figure 9:
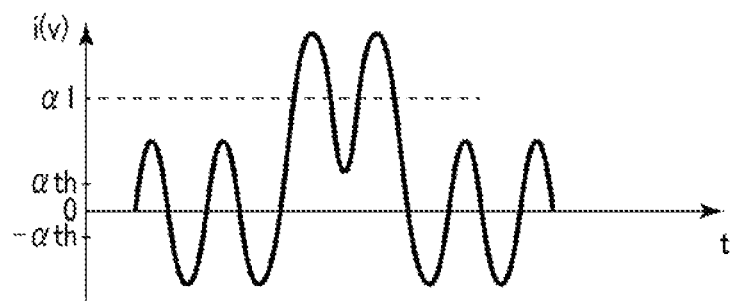
FIG. 9 is a schematic diagram depicting an example of a detected waveform of HF output detected by a current detecting circuit or a voltage detecting circuit in a case where a discharge occurs at an end effector according to the first modification.

FIG. 9 depicts an example of the detected waveform detected by the current detecting circuit 36A or the voltage detecting circuit 36B in a case where discharge has occurred at the end effector 7. In FIG. 9, an axis of abscissas indicates time t, and an axis of ordinates indicates a detected current i detected by the current detecting circuit 36A or a detected voltage v detected by the voltage detecting circuit 36B. As depicted in FIG. 9, when a discharge occurs at the end effector 7, a direct-current component is superimposed on a waveform of the output current I in the detected current i detected by the current detecting circuit 36A. Similarly, when a discharge occurs at the end effector 7, a direct-current voltage component is superimposed on a waveform of the output voltage V in the detected voltage v detected by the voltage detecting circuit 36B. Therefore, when discharge occurs at the end effector 7, the wave central value $\alpha$ is greatly shifted from zero in the detected waveform. In an example of FIG. 9, the wave of the detected waveform has a central value al in a part in which a direct-current component (direct-current voltage component) is superimposed, and the absolute value $|\alpha|$ of the central value al is larger than the threshold value $\alpha$th. In a state in which no discharge occurs at the end effector 7, on the other hand, no direct-current component (direct-current voltage component) is superimposed on the detected waveform. Therefore, the central value $\alpha$ of the wave of the detected waveform is zero, or is hardly shifted from zero.

Hence, whether or not a discharge occurs at the end effector 7 at the point in time at which the stop command is received or immediately before the point in time is determined appropriately based on whether or not the absolute value $|\alpha|$ of the central value $\alpha$ of the wave in the detected waveform at the point in time at which the stop command is received or immediately before the point in time is smaller than the threshold value $\alpha$th. Therefore, in the present modification, the processors 31 and 41 appropriately determine whether or not the end effector 7 is in contact with the biological tissue, that is, whether or not the end effector 7 is repeating contacting the biological tissue and separating from the biological tissue at high speed, by determining whether or not the absolute value $|\alpha|$ of the central value $\alpha$ in the detected waveform at the point in time at which the stop command is received or immediately before the point in time is smaller than the threshold value $\alpha$th.

As described hereinbefore, in the present modification, whether or not the end effector 7 is in contact with the biological tissue is determined appropriately based on the parameter related to the first electric energy at the point in time at which the stop command is received or immediately before the point in time. In addition, in the present modification, as in the foregoing embodiment or the like, whether or not the end effector 7 is in contact with the biological tissue is also determined appropriately based on the parameter related to the first electric energy after the point in time at which the stop command is received.

In addition, in a certain modification, a switching setting unit is disposed in one of the power supply devices 3 and 4. In this case, the switching setting unit may be disposed in one of the touch panels 38 and 48, or may be a button, a dial (not depicted), or the like disposed in one of the power supply devices 3 and 4. In the present modification, based on a setting in the switching setting unit, the processors 31 and 41 switch between a state of determining whether or not the end effector 7 is in contact with the treatment target and a state of not determining whether or not the end effector 7 is in contact with the treatment target.

In a case where the processors 31 and 41 determine whether or not the end effector 7 is in contact with the treatment target, as in the foregoing embodiment or the like, when the processors 31 and 41 receive the stop command, the processors 31 and 41 determine whether or not the end effector 7 is in contact with the treatment target based on a parameter related to the first electric energy. In a case where the processors 31 and 41 do not determine whether or not the end effector 7 is in contact with the treatment target, on the other hand, when the processors 31 and 41 receive the stop command, the processors 31 and 41 stop the output of the first electric energy and the output of the second electric energy at a point in time at which the processors 31 and 41 receive the stop command or immediately after the point in time at which the processors 31 and 41 receive the stop command. At this time, irrespective of other conditions such as whether or not the end effector is in contact with the treatment target, the output of the first electric energy and the second electric energy is stopped based on the stop command.

In addition, in a second modification, in the case where the output of the second electric energy is continued after the stop command is received, the processor 41 decreases the output of the second electric energy from the output source 43 as compared with the output of the second electric energy before the point in time at which the stop command is received. In the present modification, for example, after receiving the stop command, the processor 41 controls the output from the output source 43 by the constant current control that holds the output current I' from the output source 43 constant or substantially constant at a current value I'2 smaller than the current value I'1 with the passage of time, instead of performing the processing of S107.

Figure 10:
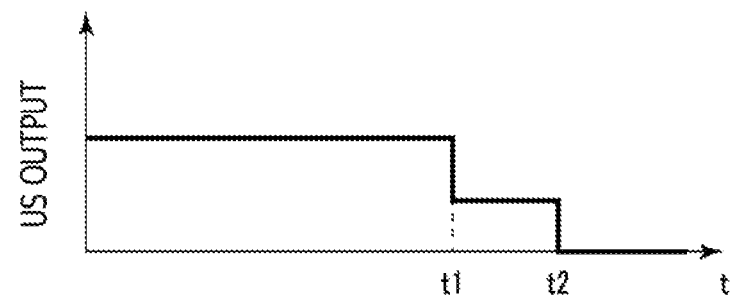
FIG. 10 is a schematic diagram depicting an example of changes in US output with the passage of time in a case where the ON-OFF state of the operating input at the operating member changes as in FIG. 4 and the impedance Z changes as in FIG. 5 in a second modification.

FIG. 10 depicts an example of changes in the US output as the output of the second electric energy from the output source 43 with the passage of time, in a case where the ON-OFF state of the operating input at an operating member (certain one of the operating buttons 17) changes as in FIG. 4 and the impedance Z changes as in FIG. 5 in the present modification. In an example depicted in FIG. 10, when the processor 41 receives the stop command at time t1 or immediately after time t1, the processor 41 decreases the output of the second electric energy (US output) as compared with the output of the second electric energy (US output) before time t1. Then, the output of the second electric energy with low power is continued until the output of the second electric energy is stopped at time t2 or immediately after time t2.

Incidentally, in another certain modification, the processor 41 decreases the output of the second electric energy as compared with the output of the second electric energy before the point in time at which the stop command is received only in a part of a period from the point in time at which the stop command is received to a point in time at which the supply of the first electric energy and the supply of the second electric energy are stopped. In this case, in a period other than the period in which the output of the second electric energy is decreased after the stop command is received, the second electric energy is output at the same level or substantially the same level as before the point in time at which the stop command is received, for example.

In addition, in a third modification, in the case where the output of the second electric energy is continued after the stop command is received, the processor 41 changes the magnitude of the output of the second electric energy from the output source 43 so as to correspond to the parameter related to the first electric energy such as the impedance Z. In other words, in the period from the point in time at which the stop command is received to the point in time at which the supply of the first electric energy and the supply of the second electric energy are stopped, the processor 41 changes the output of the second electric energy so as to correspond to the parameter related to the first electric energy. In the present modification, for example, after receiving the stop command, the processor 41 decreases the output of the second electric energy as the impedance Z is increased, that is, as the impedance Z comes closer to the threshold value Zth.

Figure 11:
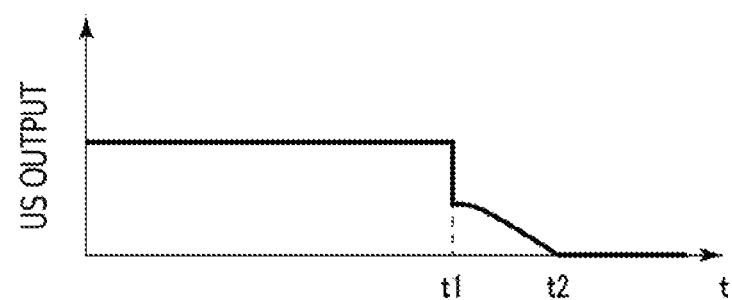
FIG. 11 is a schematic diagram depicting an example of changes in US output with the passage of time in a case where the ON-OFF state of the operating input at the operating member changes as in FIG. 4 and the impedance Z changes as in FIG. 5 in a third modification.

FIG. 11 depicts an example of changes in the US output as the output of the second electric energy from the output source 43 with the passage of time, in a case where the ON-OFF state of the operating input at an operating member (certain one of the operating buttons 17) changes as in FIG. 4 and the impedance Z changes as in FIG. 5 in the present modification. In an example depicted in FIG. 11, when receiving the stop command at time t1 or immediately after time t1, the processor 41 changes the output of the second electric energy (US output) so as to correspond to the impedance Z. In an example of FIG. 5, the impedance Z increases with the passage of time, in the period from time t1 to time t2. Therefore, as depicted in FIG. 11, in the period between time t1 and time t2, the processor 41 decreases the output of the second electric energy with the passage of time so as to correspond to the increase in the impedance Z with the passage of time. Then, when the impedance Z reaches the threshold value Zth at time t2, the output of the first electric energy and the output of the second electric energy are stopped at time t2 or immediately after time t2, as in the foregoing embodiment or the like.

In addition, in a certain modification, for example, one of the power supply devices 3 and 4 has a sound generator such as a buzzer. When the processors 31 and 41 receive the stop command, the processors 31 and 41 make a notification by issuing a sound from the sound generator. In addition, the processors 31 and 41 also make a notification by issuing a sound from the sound generator when determining that the end effector 7 is not in contact with the biological tissue and stopping the output of the first electric energy and the second electric energy after receiving the stop command. Incidentally, the sound issued when the stop command is received and the sound issued when the output is stopped may be identical to each other, or may be different from each other. In addition, a notification may be made by making a light emitting member such as a light emit light in place of the sound generator, or a notification may be made by display on one of the touch panels 38 and 48.

In addition, in the foregoing embodiment or the like, two power supply devices 3 and 4 are arranged. However, in a certain modification, the output sources 33 and 43 may be arranged in one power supply device. In this case, for example, the power supply device having the output sources 33 and 43 includes the current detecting circuits 36A and 46A, the voltage detecting circuits 36B and 46B, and the A/D converters 37 and 47, and includes one or a plurality of processors. The processing performed by the processors 31 and 41 in the foregoing embodiment or the like is performed by the one or plurality of processors included in the power supply device. Hence, the one or plurality of processors included in the power supply device form the control device controlling the treatment system 1.

In addition, in a certain modification, the treatment instrument 2 includes an electric motor in place of the ultrasonic transducer 21, as an electric element. In the present modification, the second electric energy output from the output source 43 is supplied to the electric motor. The electric motor is actuated by supplying the second electric energy to the electric motor, and the electric motor generates a driving force. Then, the driving force generated in the electric motor is transmitted to the end effector 7. The end effector 7 is operated by the transmitted driving force. Hence, also in the present modification, the end effector 7 is operated by actuating the electric motor by the supply of the second electric energy to the electric motor as an electric element.

In the foregoing embodiment or the like, in the treatment instrument (2), the end effector (7) becomes able to apply the high frequency current to the biological tissue by being supplied with the first electric energy. The end effector (7) is operated by actuating the electric element (21) by the supply of the second electric energy. The processors (31, 41) of the control device receive the stop command to stop the supply of the first electric energy and the second electric energy in a state in which the first electric energy and the second electric energy are supplied. Then, the processors (31, 41) determine whether or not the end effector is in contact with the biological tissue based on a parameter (Z; 1; P; α) related to the first electric energy after receiving the stop command.

It is to be noted that the invention of the present application is not limited to the foregoing embodiments and can be modified variously without departing from the spirit of the invention in an implementation stage. In addition, the embodiments may be combined with each other and carried out as appropriate wherever possible, and effects of the combinations are obtained in that case. Further, the foregoing embodiments include inventions in various stages, and various inventions can be extracted by appropriate combinations in a plurality of constituent elements disclosed.

In sum, one aspect of the disclosed technology is directed to a treatment system comprises a power supply apparatus and a treatment instrument configured to communicate electrically with the power supply apparatus so as to perform a treatment on a biological tissue. The treatment instrument includes an end effector that transmits a high-frequency current delivered by a first electrical energy to the biological tissue. An electric element is configured to operate the end effector by being actuated using second electric energy. The power supply apparatus includes a processor configured to receive a stop command to cutoff the supply of the first electric energy and the second electric energy in a state in which the first electric energy and the second electric energy are supplied and determine whether or not the end effector is in contact with the biological tissue based on a parameter related to the first electric energy after receiving the stop command.

When the processor determines that the end effector is in contact with the biological tissue, the processor makes operation of the end effector continued by continuing the supply of the second electric energy to the electric element. When the processor determines that the end effector is not in contact with the biological tissue, the processor stops the supply of the first electric energy to the end effector and the supply of the second electric energy to the electric element. The processor decreases output of the first electric energy to the end effector based on reception of the stop command. The processor determines whether or not the end effector is in contact with the biological tissue based on the parameter after a point in time at which the processor decreases the output of the first electric energy. The processor determines whether or not the end effector is in contact with the biological tissue based on the parameter at a point in time at which the processor receives the stop command or immediately before the point in time. The processor decreases output of the first electric energy to the end effector when determining that the end effector is in contact with the biological tissue based on the parameter at the point in time at which the processor receives the stop command or immediately before the point in time. The processor determines whether or not the end effector is in contact with the biological tissue based on the parameter after a point in time at which the processor decreases the output of the first electric energy. The processor determines whether or not the end effector is in contact with the biological tissue by using, as the parameter, at least one of an output current to the end effector, an output power to the end effector, and an impedance of a circuit through which the output current flows. The processor decreases output of the second electric energy as compared with the output of the second electric energy before a point in time at which the processor receives the stop command in at least a part of a period from the point in time at which the processor receives the stop command to a point in time at which the processor stops the supply of the first electric energy and the supply of the second electric energy.

The processor changes output of the second electric energy so as to correspond to a change in the parameter in a period from a point in time at which the processor receives the stop command to a point in time at which the processor stops the supply of the first electric energy and the supply of the second electric energy. The electric element is an ultrasonic transducer. The electric element is an electric motor. The processor is configured to electrically communicate with the end effector so as to transmit an ultrasonic vibration generated by an ultrasonic transducer as defined by the electric element using the second electric energy.

Another aspect of the disclosed technology is directed to a method of operating a treatment system in conjunction with a treatment instrument including an end effector configured to apply a high frequency current to a biological tissue delivered by a first electric energy and an electric element configured to operate the end effector by generating ultrasonic vibration delivered by a second electrical energy. The method comprises receiving a stop command to cutoff the supply of the first electric energy and the second electric energy in a state in which the first electric energy and the second electric energy are supplied and determining whether or not the end effector is in contact with the biological tissue based on a parameter related to the first electric energy after receiving the stop command.

A further aspect of the disclosed technology is directed to a method of operating a treatment instrument of comprises an end effector applying a high frequency current to a biological tissue, the end effector applying an ultrasonic vibration to the biological tissue by transmitting the ultrasonic vibration; and in a state of treating the biological tissue by applying the high frequency current and the ultrasonic vibration to the biological tissue, applying the ultrasonic vibration to the biological tissue and detecting whether or not the end effector is in contact with the biological tissue after completion of treatment of the biological tissue, and stopping the ultrasonic vibration when determining that the end effector is not in the contact.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A treatment system comprising: a power supply apparatus; and a treatment instrument configured to communicate electrically with the power supply apparatus so as to perform a treatment on a biological tissue wherein the treatment instrument having an end effector that transmits a high-frequency current delivered by a first electrical energy to the biological tissue, and an electric element configured to operate the end effector by being actuated using second electric energy and wherein the power supply apparatus includes a processor configured to: receive a stop command when a switch is made from an operating state in which an operating input is provided by one operating button to a non-operating state in which no operating input is provided by any operating buttons; upon receiving the stop command, decrease output of the first electric energy to the end effector to a non-zero value while continuing the supply of the second electric energy to the electric element to maintain operation of the end effector; and determine whether or not the end effector is in contact with the biological tissue based on a parameter related to the first electric energy.

2. The treatment system of claim 1, wherein when the processor determines that the end effector is not in contact with the biological tissue, the processor stops the supply of the first electric energy to the end effector and the supply of the second electric energy to the electric element.

3. The treatment system of claim 1, wherein the processor determines whether or not the end effector is in contact with the biological tissue based on the parameter after a point in time at which the processor decreases the output of the first electric energy.

4. The treatment system of claim 1, wherein the processor determines whether or not the end effector is in contact with the biological tissue based on the parameter at a point in time at which the processor receives the stop command or immediately before the point in time.

5. The treatment system of claim 4, wherein the processor decreases output of the first electric energy to the end effector when determining that the end effector is in contact with the biological tissue based on the parameter at the point in time at which the processor receives the stop command or immediately before the point in time, and the processor determines whether or not the end effector is in contact with the biological tissue based on the parameter after a point in time at which the processor decreases the output of the first electric energy.

6. The treatment system of claim 1, wherein the processor determines whether or not the end effector is in contact with the biological tissue by using, as the parameter, at least one of an output current to the end effector, an output power to the end effector, and an impedance of a circuit through which the output current flows.

7. The treatment system of claim 1, wherein the processor decreases output of the second electric energy as compared with the output of the second electric energy before a point in time at which the processor receives the stop command in at least a part of a period from the point in time at which the processor receives the stop command to a point in time at which the processor stops the supply of the first electric energy and the supply of the second electric energy.

8. The treatment system of claim 1, wherein the processor changes output of the second electric energy so as to correspond to a change in the parameter in a period from a point in time at which the processor receives the stop command to a point in time at which the processor stops the supply of the first electric energy and the supply of the second electric energy.

9. The treatment system of claim 1, wherein the electric element is an ultrasonic transducer.

10. The treatment system of claim 1, wherein the electric element is an electric motor.

11. The treatment system of claim 1, wherein the processor configured to electrically communicate with the end effector so as to transmit an ultrasonic vibration generated by an ultrasonic transducer as defined by the electric element using the second electric energy.

12. The treatment system of claim 1, wherein the processor is configured to decrease the output of the first electric energy, from output by which the biological tissue is to be coagulated and/or incised to lower output in which whether or not the end effector is in contact with the biological tissue can be determined, based on the reception of the stop command.

13. The treatment system of claim 12, wherein the power supply apparatus output the second electric energy as an energy by which the end effector is vibrated so as to prevent the biological tissue from sticking to the end effector.

14. The treatment system of claim 1, wherein the power supply apparatus output the second electric energy as an energy by which the end effector is vibrated so as to prevent the biological tissue from sticking to the end effector.

15. A method of operating a treatment system in conjunction with a treatment instrument including an end effector configured to apply a high frequency current to a biological tissue delivered by a first electric energy and an electric element configured to operate the end effector by generating ultrasonic vibration delivered by a second electrical energy, the method comprising: receiving a stop command when a switch is made from an operating state in which an operating input is provided by one operating button to a non-operating state in which no operating input is provided by any operating button; upon receiving the stop command, decreasing output of the first electric energy to the end effector to a non-zero value while continuing the supply of the second electric energy to the electric element to maintain operation of the end effector; and determining whether or not the end effector is in contact with the biological tissue based on a parameter related to the first electric energy.

* * * * *